US009488579B2

(12) United States Patent
Bjornson et al.

(10) Patent No.: US 9,488,579 B2
(45) Date of Patent: *Nov. 8, 2016

(54) OPTICAL MEASURING APPARATUS AND METHOD FOR THE ANALYSIS OF SAMPLES CONTAINED IN LIQUID DROPS

(71) Applicant: TECAN TRADING AG, Mannedorf (CH)

(72) Inventors: Torleif Ove Bjornson, Gilroy, CA (US); Thomas Geiges, Mannedorf (CH)

(73) Assignee: TECAN TRADING AG, Mannedorf (CH)

( * ) Notice: Subject to any disclaimer, the term of this patent is extended or adjusted under 35 U.S.C. 154(b) by 90 days.

This patent is subject to a terminal disclaimer.

(21) Appl. No.: 14/538,422

(22) Filed: Nov. 11, 2014

(65) Prior Publication Data

US 2015/0060700 A1 Mar. 5, 2015
US 2016/0266040 A2 Sep. 15, 2016

Related U.S. Application Data

(63) Continuation of application No. 13/746,722, filed on Jan. 22, 2013, now Pat. No. 8,912,007.

(51) Int. Cl.
*G01N 21/17* (2006.01)
*G01N 21/03* (2006.01)
(Continued)

(52) U.S. Cl.
CPC ............ *G01N 21/64* (2013.01); *B01L 3/0241* (2013.01); *G01N 1/28* (2013.01); *G01N 21/01* (2013.01);
(Continued)

(58) Field of Classification Search
CPC . B01L 3/021; B01L 3/0241; G01N 15/0227; G01N 2015/0038; G01N 2015/0693; G01N 2021/0314; G01N 2021/035; G01N 2021/8564; G01N 2021/0162; G01N 2035/1046; G01N 2035/1062; G01N 21/01; G01N 21/03; G01N 21/17; G01N 21/33; G01N 21/49; G01N 21/645; G01N 21/64; G01N 21/59; G01N 21/6486; G01N 1/28; G01N 2201/0612; G01N 2201/062; G01N 2201/08; Y10T 436/11; Y10T 436/119163; Y10T 436/143333; Y10T 436/2575
USPC ............... 422/501, 509, 521, 524, 67, 68.1, 422/82.05, 82.08, 82.09; 435/287.2, 288.7; 436/164, 165, 172, 180, 43, 54, 94; 250/227.11, 458.1, 459.1, 461.1, 372, 250/564
See application file for complete search history.

(56) References Cited

U.S. PATENT DOCUMENTS 3,734,622 A * 5/1973 Adler ..................... G01N 21/86 356/246
4,643,580 A * 2/1987 Gross ................. G01N 21/0303 250/576

(Continued)

FOREIGN PATENT DOCUMENTS

EP 0144928 11/1984
GB 2280954 A 2/1995

OTHER PUBLICATIONS

Bochkarev N N et al, Fluorescence of a Liquid Drop with a Dye Excited by Femtosecond Laser Pulses, Russian Physics Journal, Kluwer Academic Publishers—Plenum Publishers, NE, vol. 48, No. 4, Apr. 2005, pp. 344-348.

(Continued)

*Primary Examiner* — Maureen Wallenhorst
(74) *Attorney, Agent, or Firm* — Notaro, Michalos & Zaccaria P.C.

(57) ABSTRACT

An optical measuring apparatus and method for analysis of samples contained in liquid drops provided by a liquid handling system has a liquid handling tip. A light source irradiates the liquid drop; a detector measures sample light; and an optics system with first optical elements transmits irradiation light, and a processor processes the measurement signals. The liquid drop is suspended at the liquid handling orifice of the liquid handling tip in a position where the liquid drop is penetrated by a first optical axis defined by the light source and the first optical elements. The liquid drop is physically touched only by the liquid handling tip and the liquid sample inside the liquid handling tip. A mutual adaption of the size and position of the liquid drop with respect to the first optical elements is achieved.

25 Claims, 3 Drawing Sheets

Figure 6A:
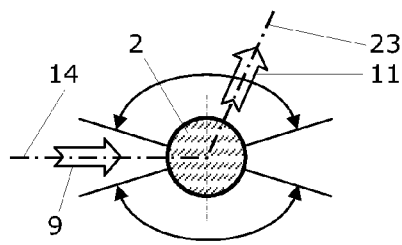

(51) Int. Cl.
| | |
|---|---|
| *G01N 21/13* | (2006.01) |
| *G01N 21/64* | (2006.01) |
| *G01N 21/59* | (2006.01) |
| *G01N 35/00* | (2006.01) |
| *C12Q 1/68* | (2006.01) |
| *G01N 1/28* | (2006.01) |
| *G01N 21/01* | (2006.01) |
| *G01N 21/33* | (2006.01) |
| *B01L 3/02* | (2006.01) |
| *G01N 21/85* | (2006.01) |
| *G01N 35/10* | (2006.01) |

(52) U.S. Cl.
CPC .............. *G01N 21/17* (2013.01); *G01N 21/33* (2013.01); *G01N 21/645* (2013.01); *B01L 3/021* (2013.01); *G01N 21/6486* (2013.01); *G01N 2021/035* (2013.01); *G01N 2021/0314* (2013.01); *G01N 2021/8564* (2013.01); *G01N 2035/1046* (2013.01); *G01N 2035/1062* (2013.01); *G01N 2201/062* (2013.01); *G01N 2201/0612* (2013.01); *G01N 2201/08* (2013.01); *Y10T 436/11* (2015.01); *Y10T 436/119163* (2015.01); *Y10T 436/143333* (2015.01); *Y10T 436/2575* (2015.01)

(56) References Cited

U.S. PATENT DOCUMENTS

| | | | |
|---|---|---|---|
| 4,910,402 A | | 3/1990 | McMillan |
| 4,936,828 A | | 6/1990 | Chiang |
| 5,766,959 A | * | 6/1998 | Dasgupta .............. B01L 3/0241 422/504 |
| 6,137,571 A | | 10/2000 | Johnson |
| 6,809,826 B2 | * | 10/2004 | Robertson .............. B82Y 15/00 356/246 |
| 8,912,007 B2 | * | 12/2014 | Bjornson .............. B01L 3/0241 422/501 |
| 2013/0201471 A1 | | 8/2013 | Bui et al. |

OTHER PUBLICATIONS

McMillan, et al, Quantitative Drop Spectroscopy Using the Drop Analyser: Theoretical and Experimental Approach for Microvolume Applications and Non-turbid Solutions: Quantitative Drop Spectroscopy Using the Drop Analyser, Measurement Science and Technology, IOP, Bristol, GB, vol. 19, No. 5, May 2008, p. 55681.
International Search Report for PCT/EP2014/050301 filed Jan. 9, 2014.

* cited by examiner

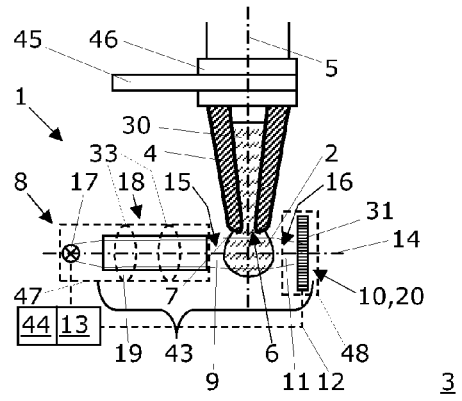

OPTICAL MEASURING APPARATUS AND METHOD FOR THE ANALYSIS OF SAMPLES CONTAINED IN LIQUID DROPS

RELATED PATENT APPLICATIONS

This is a Continuation application to U.S. Ser. No. 13/746,722 that has been filed on Jan. 22, 2013, now U.S. Pat. No. 8,912,007, the entire disclosure of this application is herein incorporated by explicit reference.

FIELD OF TECHNOLOGY

The present invention relates to an optical measuring apparatus and also to an optical measuring method for the analysis of samples contained in liquid drops that are provided by liquid handling systems. Such liquid handling systems typically comprise at least one liquid handling tip with a liquid handling axis and with a liquid handling orifice at a distal end of the liquid handling tip. The liquid handling axis of such liquid handling tips usually is extending inside the liquid handling tip and penetrating the liquid handling orifice. The optical measuring apparatus comprises a light source that is configured for providing irradiation light for irradiating a liquid drop. The optical measuring apparatus also comprises a detector that is configured for measuring sample light arriving from said liquid drop. Preferably for carrying out the method according to the invention, an optical measuring apparatus is combined with an appropriate liquid handling system.

RELATED PRIOR ART

Automated liquid handling systems are generally well known in the art and utilized e.g. in biological and biochemical laboratories. An example is the Freedom EVO® robotic workstation from the present applicant (Tecan Schweiz AG, Seestrasse 103, CH-8708 Mannedorf, Switzerland). This device enables automated liquid handling in automated connection with an analytical system. These automated systems typically are capable to provide larger volumes of liquids (microliter to milliliter) to process. However, also very small volumes of liquids (picoliter to nanoliter) can be pipetted (aspirated and dispensed) or dispensed with such automated liquid handling systems. Such automated liquid handling systems are particularly suitable for attaching the apparatus or for carrying out the method of the present invention.

From the patent EP 0 144 928 B1, a photometric head for small sample volumes is known. This photometric head comprises a light transmitter and a light receiver, each comprising a light guide. The surface for the emergence of light energy of the light transmitter light guide is arranged in a distance to the surface of the light guide of the light receiver for the entrance of light energy. This distance is defining a narrow gap for accommodating a liquid sample. The liquid sample is held in this gap by direct contact to the two surfaces of the light guides that form the gap. A liquid sample is provided to the gap by a separate applicator (such as e.g. a dispenser needle).

From the U.S. Pat. No. 4,910,402, an apparatus and method for measuring a property of a liquid is known. This apparatus comprises at least one guide for electromagnetic radiation, means for directing electromagnetic radiation into the guide, means for providing at least one drop of liquid in contact with the guide at a position where radiation from the guide can enter the drop, and means for deriving a signal which is a function of the interaction of the radiation with the liquid of the drop.

These documents disclose photometric heads or light guides that provide for the advantage that there is no need for using cuvettes with their well known disadvantages in optical measuring, i.e.:
- large sample volumes in the range of 1 ml are needed for achieving the desired filling level in the measurement cuvette;
- all measurements of a an entire assay must be carried out within the same cuvette, because mass tolerances of different cuvettes would greatly influence the results of the measurements;
- the cuvette has to be thoroughly cleaned after each measurement, or contamination and carryover problems are to be expected.

However, the surfaces of the respective light guides also need to be thoroughly cleaned after each measurement in order to avoid carryover and cross contamination of samples and are thus not well suited for e.g. automated analysis of samples contained in liquid drops that are provided by liquid handling systems.

OBJECTS AND SUMMARY OF THE PRESENT INVENTION

It is a first object of the present invention to suggest an alternative optical measuring apparatus for the analysis of samples contained in liquid drops that are provided by liquid handling systems.

This first object is achieved by suggesting an optical measuring apparatus configured for the analysis of samples contained in liquid drops that are provided by a liquid handling system which comprises at least one liquid handling tip with a liquid handling axis and with a liquid handling orifice at a distal end of the liquid handling tip, the liquid handling axis extending inside the liquid handling tip and penetrating the liquid handling orifice; the optical measuring apparatus comprising a light source configured for providing irradiation light for irradiating a liquid drop of a liquid sample; a detector configured for measuring sample light arriving from said liquid drop and for providing measurement signals that represent the measured sample light; an optics system with first optical elements for transmitting the irradiation light, and a processor connected to the detector and configured to accept and process the measurement signals provided by the detector, wherein the light source and the liquid drop define a first optical axis of the first optical elements of the optics system that extends essentially perpendicular to the liquid handling axis, the liquid drop being provided by the liquid handling system and being suspended at the liquid handling orifice of the liquid handling tip in a position where the liquid drop is penetrated by the first optical axis, wherein the liquid drop is physically separated from the optics system of the optical measuring apparatus and is physically touched only by the liquid handling tip of the liquid handling system and the liquid sample inside the liquid handling tip, the light source with the first optical elements being thus separated from the liquid drop by a first air space and the detector being thus separated from the liquid drop by a second air space.

Preferably, the size and position of the liquid drop as well as the first optical element and/or a second optical element of the optics system are already mutually adapted for achieving the highest signal/noise ratio. As an also preferred alternative, the optical measuring apparatus comprises means for mutual adaption of the size and/or position of the liquid drop with respect to the first and/or second optical elements of the optics system.

It is a second object of the present invention to suggest an alternative optical measuring method for the analysis of samples contained in liquid drops that are provided by liquid handling systems.

This second object is achieved by providing an optical measuring method of analyzing samples contained in liquid drops that are provided by liquid handling systems, wherein the method comprises the steps of:

(a) providing a liquid handling system which comprises at least one liquid handling tip with a liquid handling axis and with a liquid handling orifice at a distal end of the liquid handling tip, the liquid handling axis extending inside the liquid handling tip and penetrating the liquid handling orifice;
(b) providing a liquid drop that is suspended at the liquid handling orifice of the liquid handling tip of the liquid handling system in a position where the liquid drop is penetrated by a first optical axis that extends essentially perpendicular to the liquid handling axis;
(c) providing an optical measuring apparatus that comprises a light source, a detector, and an optics system with first optical elements for transmitting irradiation light from the light source to the liquid drop and with second optical elements for transmitting sample light from the liquid drop to the detector; the irradiation source and the liquid drop defining the first optical axis of the first optical elements of the optics system; a first and second air space separating the liquid drop from the light source and detector and their associated first and second optical elements that thus do not contact the liquid drop;
(d) irradiating the liquid drop with irradiation light originating from the light source;
(e) measuring sample light arriving from the liquid drop and providing measurement signals with the detector; and
(f) processing with a processor that is operatively connected to the detector the measurement signals provided by the detector.

Optionally, a step (g) may be carried out in addition, wherein an amount of a sample to be delivered is adjusted, the adjustment being based on the result of the measurement that is provided by the step (f).

Additional and inventive features derive from the dependent claims in each case.

In the context of the present invention, the following definitions apply:

A "liquid handling system" can be selected from the group comprising a workstation for robotic sample processing equipped with at least one liquid handling robot, a standalone apparatus equipped with at least one liquid handling tip, and a handheld liquid handling device equipped with at least one liquid handling tip.

A "liquid handling tip" can be selected form the group comprising a pipette tip and a dispenser tip.

A "pipette tip" or "dispenser tip" may refer to a disposable tip (e.g. from polypropylene), to a needle (e.g. made from a synthetic material or from a metal), to a syringe needle as well as to any other hollow tool for transferring or distributing liquid samples.

"Pipetting" refers to aspiration (uptake) and dispense (distribution) of liquids and liquid samples.

"Dispensing" refers to the distribution of liquids and liquid samples.

A "receiver" preferably comprises one of a photodiode, photomultiplier, and a CCD or CMOS chip.

ADVANTAGES OF THE PRESENT INVENTION COMPRISE

The invention provides a detector for determining optical properties of samples contained in liquid drops while the drop with the sample is still attached to a pipette tip, dispenser tip, or needle probe of a liquid handling robot.

The liquid with the sample is already inside of the pipette tip, dispenser tip, or needle probe of a liquid handling robot; optical analysis of the sample can thus be performed during the process of pipetting or dispensing samples contained in liquid drops.

Only a few microliters of liquid are necessary for creating the small volume drop that is containing the sample to be analyzed.

In the cited prior art, there is an inherent loss of sample liquid (often rare or expensive) due to the need to contact the light guide surface with the drop; such inherent loss is eliminated by the current invention because there is no contact between the drop and the light guides.

A wide variety of optical parameters of samples contained in liquid drops can be investigated, including the absorbance of light ranging from ultra violet to infrared, fluorescence measurements, and luminescence measurements.

By not measuring through the tip, absorbance, fluorescence, and optical aberrations from the tip itself are eliminated and cannot influence the measurement.

By not contacting the sample to a particular surface apart from a pipette tip or needle probe, carryover and sample loss are avoided and the sample can be aspirated back into the pipette tip or needle probe.

Fully automated measurement or analysis of a liquid sample is possible, because there is no manual cleaning step necessary when using the optical measuring apparatus of the present invention.

BRIEF INTRODUCTION OF THE DRAWINGS

Figure 6B:
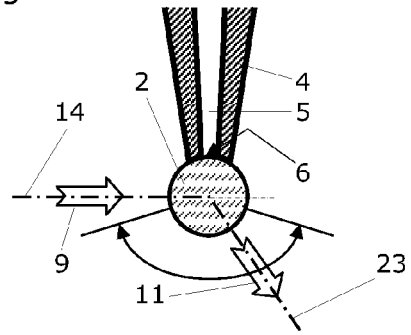
Figure 7:
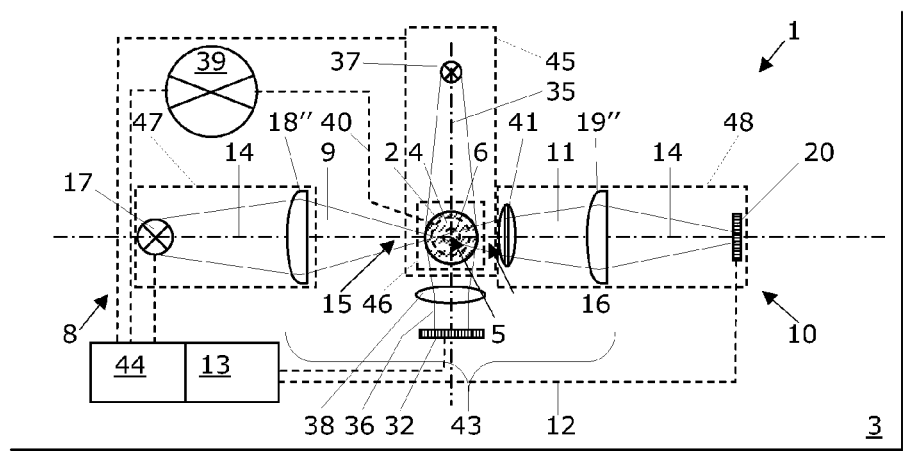
Figure 8:
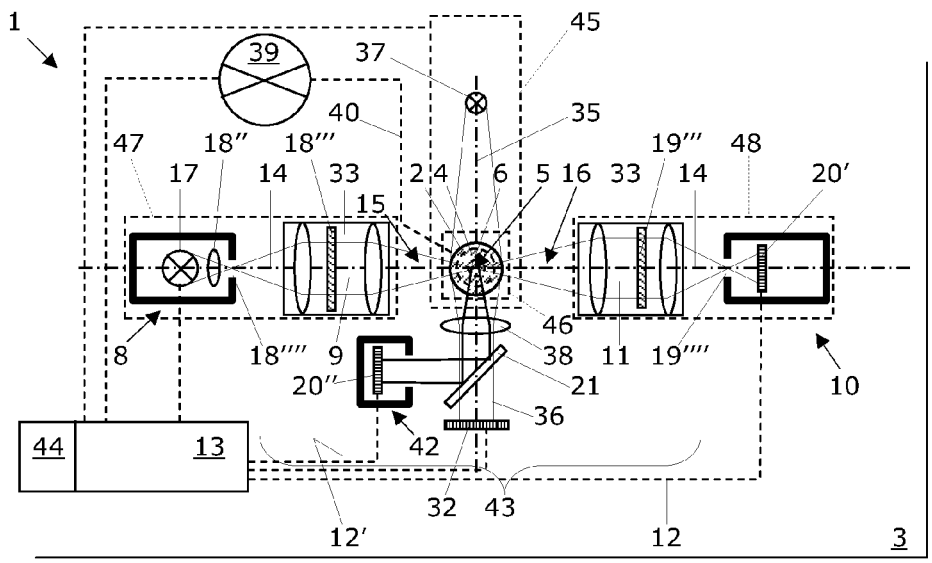
Figure 9:
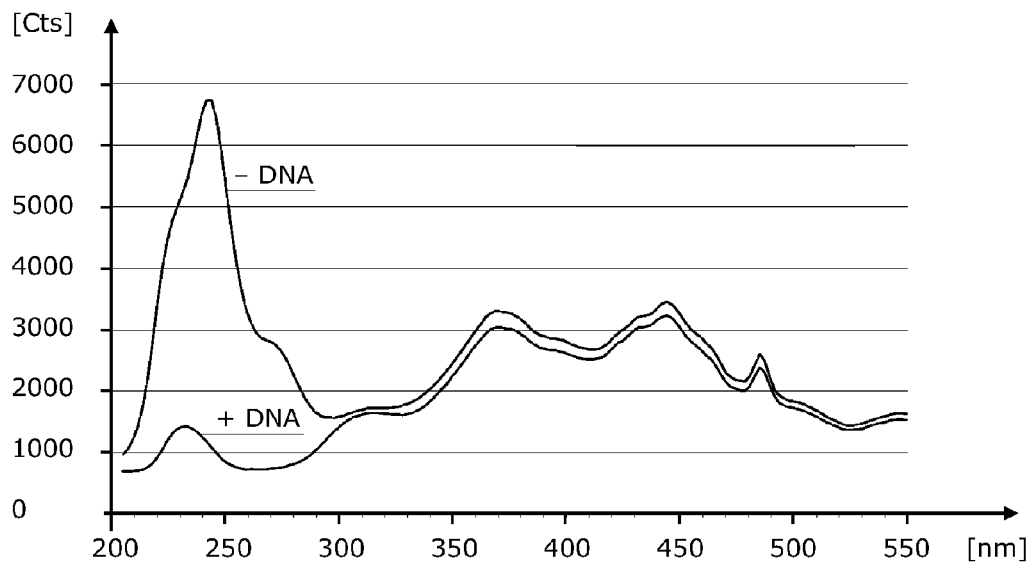
Figure 10:
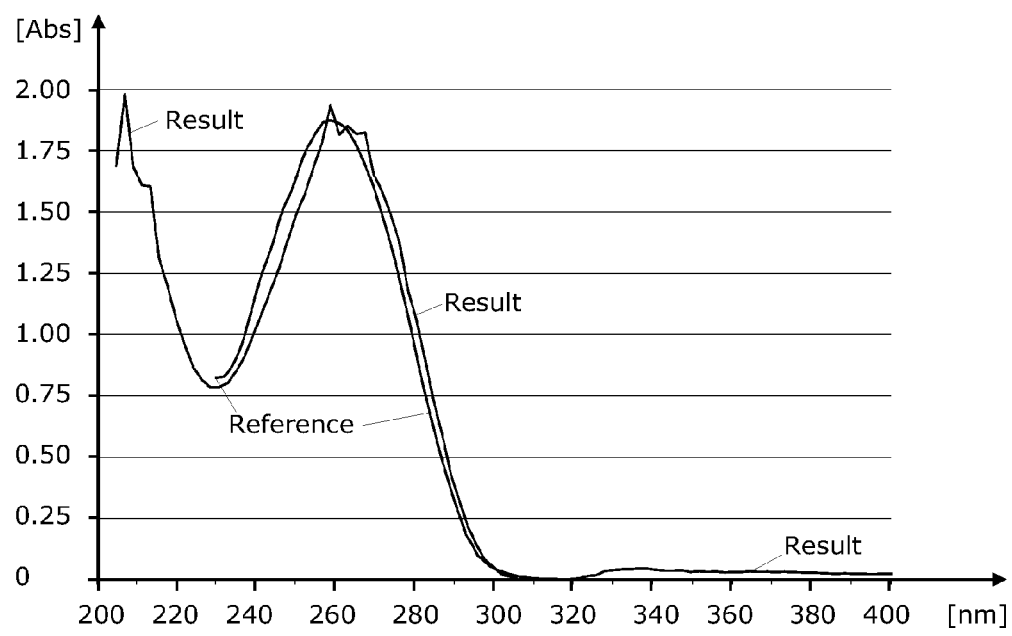

The optical measuring apparatus and the optical measuring method for the analysis of samples contained in liquid drops that are provided by liquid handling systems according to the present invention are now explained in more detail with the help of the attached schematic drawings that show preferred, exemplary embodiments of the invention and that are not intended to narrow the scope of the invention. It is shown in:

FIG. 1 a vertical cross section through a liquid handling tip holding at its orifice a suspended liquid drop in a position between a light source and a detector of an optical measuring apparatus according to a first embodiment;

FIG. 2 a vertical cross section through a liquid handling tip holding at its orifice a suspended liquid drop in a position between a light source and a detector of an optical measuring apparatus according to a second embodiment;

FIG. 3 a vertical cross section through a liquid handling tip holding at its orifice a suspended liquid drop in a position between a light source and a detector of an optical measuring apparatus according to a third embodiment;

FIG. 4 a vertical cross section through a liquid handling tip holding at its orifice a suspended liquid drop in a position between a light source and a detector of an optical measuring apparatus according to a fourth embodiment;

FIG. 5 a horizontal projection of the optical measuring apparatus according to a fifth embodiment comprising a light source and a detector, the liquid handling system providing a liquid drop suspended from the orifice of a liquid handling tip and positioned in between the light source and the detector;

FIG. 6A a horizontal projection of the situation of the liquid drop to be investigated, with indicated preferred ranges for fluorescence or luminescence detection;

FIG. 6B a vertical section view of the situation of the liquid drop to be investigated, with indicated preferred range for fluorescence or luminescence detection;

FIG. 7 a horizontal projection of the optical measuring apparatus according to a sixth embodiment comprising a light source and a detector, the liquid handling system providing a pump to vary the size of a liquid drop suspended from the orifice of a liquid handling tip and positioned in between the light source and the detector;

FIG. 8 a horizontal projection of the optical measuring apparatus according to a seventh embodiment comprising a light source and a detector, the liquid handling system providing a fluorescence or luminescence detector for measuring fluorescence or luminescence emitted by the sample in the liquid drop suspended from the orifice of a liquid handling tip and positioned in between the light source and the detector;

FIG. 9 a comparison of absorbance spectra (unprocessed raw signals) of a buffer drop with DNA and a buffer drop without DNA as captured with the optical measuring apparatus of the present invention;

FIG. 10 a comparison of absorbance spectra (processed raw signals) of the same DNA sample in buffer as captured with the optical measuring apparatus of the present invention or captured with a conventional spectrometer.

DESCRIPTION OF PREFERRED EMBODIMENTS OF THE INVENTION

The FIG. 1 shows a vertical cross section through a liquid handling tip holding at its orifice a suspended liquid drop in a position between a light source and a detector of an optical measuring apparatus according to a first embodiment. The optical measuring apparatus 1 according to the first embodiment is configured for the analysis of samples contained in liquid drops 2 that are provided by liquid handling systems 3 which comprise at least one liquid handling tip 4 with a liquid handling axis 5 and with a liquid handling orifice 6 at a distal end 7 of the liquid handling tip 4.

Usually and preferably, the liquid handling axis 5 extends in a vertical direction and perpendicular to a horizontal plane. Minor deviations from an exact vertical direction could be tolerated especially in a case where the overall shape of the liquid drops 2 is spherical. The liquid handling axis 5 extends inside the liquid handling tip 4 of the liquid handling system 3 and penetrates the liquid handling orifice 6. Such liquid handling tips 4 normally are straight and of a slim configuration in order to enable accession to a well of a standard microplate with e.g. 24, 96, 384, or 1536 wells according to the ANSI standard. Thus, the liquid handling tip 4 preferably extends in a substantially vertical direction too.

The optical measuring apparatus 1 comprises a light source 8 that is configured for providing irradiation light 9 for irradiating a liquid drop 2. Preferably, the light source 8 comprises a light emitting device 17 that is selected from the group comprising an arc lamp 17', a laser, and a light emitting diode 17" (LED). Such LEDs also comprise laser diodes. It is further preferred that the light source 8 comprises at least one first optical element 18 that is selected from the group comprising an optic fiber 18' or fiber bundle, a lens 18", a filter 18''', a slit or pinhole 18'''', and a monochromator.

The optical measuring apparatus 1 also comprises a detector 10 that is configured for measuring sample light 11 arriving from said liquid drop 2 and for providing measurement signals 12 that represent the measured sample light 11. Preferably, the detector 10 comprises at least one second optical element 19 that is selected from the group comprising an optic fiber 19' or fiber bundle (see FIG. 5), a lens 19'' (see FIG. 3), a filter 19''' (see FIG. 2), a slit or pinhole 19'''' (see FIG. 5), and a monochromator. It is further preferred that the detector 10 comprises a light receiver 20 that is selected from the group comprising a photodiode 20', a photomultiplier chip 20'', a photomultiplier tube 20''', a CCD chip, and a CMOS chip 20'.

The optical measuring apparatus 1 also comprises a processor 13 that is connected to the detector 10 and that is configured to accept and process the measurement signals 12 provided by the detector 10. Preferably, the processor 13 of the optical measuring apparatus 1 comprises an algorithm that is configured for calculating an actual optical pathlength of the light penetrating the liquid drop 2. This algorithm can be stored in a memory of the processor 13 or on a portable data store, such as a compact disc (CD) or digital versatile disc (DVD). For calculating an actual optical pathlength of the light penetrating the liquid drop 2, the algorithm is first loaded into the processor 13 or at least activated in the processor 13.

The optical measuring apparatus 1 according to the first embodiment of the present invention is characterized in that the light source 8 and the detector 10 define a first optical axis 14 that extends essentially perpendicular to the liquid handling axis 5. According to the explanation above, it is preferred that the first optical axis 14 extends in a substantial horizontal direction. Further according to the present invention, the light source 8 and the detector 10 are located contact-free with respect to a liquid drop 2 that is provided by the liquid handling system 3 and that is suspended at the liquid handling orifice 6 of the liquid handling tip 4 of the liquid handling system 3. In preference, the light source 8 and the detector 10 are coaxially located on the first optical axis 14 and in a position that the liquid drop 2 can be positioned to be penetrated by the first optical axis 14. Because of their location, the light source 8 is separated from the liquid drop 2 by a first air space 15 and the detector 10 is separated from the liquid drop 2 by a second air space 16. In other words, the light source 8 and the detector 10 do not touch the liquid drop 2 with the sample to be analyzed. In consequence, the liquid drop 2 only is in physical contact with the liquid handling orifice 6 of the liquid handling tip 4 of the liquid handling system 3 and with sample liquid that is kept inside the liquid handling tip 4, the liquid drop 2 being a part of that sample liquid.

Typical for the first embodiment of the inventive optical measuring apparatus as depicted in FIG. 1 is a light source 8 that comprises a light emitting device 17 in the form of at least one laser diode. Laser diodes are known to deliver light of a particular wavelength. If within short time intervals (e.g. within fractures of a second) light of two different wavelengths is needed, two corresponding laser diodes are preferably provided together with a switch that connects an optical light guide 18 with one or the other laser diode for coupling its light into the light guide. Alternatively (and preferably if two or more laser diodes are used), separate light guides could be used for each individual source emitting light of a particular wavelength. Laser diodes are rather atypical for certain wavelengths. In such cases and preferably, Xenon Flash lamps or Deuterium Lamps are used as light emitting devices 17. In order to achieve preferred monochromatic irradiation of the drop 2 to be inspected, filters and/or a monochromator are used. Scans of the spectrum over a wide range of wavelengths are possible too.

For e.g. calculating the concentration of DNA or RNA in a droplet (irradiation light at 260/280 nm is necessary), use of a monochromator with a band-pass filter or laser diodes with light of the particular wavelengths is sufficient and a filter (not shown in FIG. 1) can be dispensed with. On the other side of the suspended liquid drop 2, the detector 10 is placed and preferably in the simple first embodiment, a filter (not shown in FIG. 1) can be dispensed with for the detector too. It is preferred that at least the detector 10 is operatively connected to the processor 13 of the optical measuring apparatus 1 in order to feed measurement signals 12 into the processor 13. It is further preferred that the processor 13 is also operatively linked with the light emitting device and/or a switch that connects the optical light guide 18 with one or the other laser diode; in consequence, the measurement signals 12 received from the detector 10 can be correlated to the light source 8 that induced these measurement signals. Alternatively (and preferably if light with two or more different wavelengths is used), separate light guides could be use for each individual detector 20 receiving light of a particular wavelength.

Alternatively, instead of an optical light guide, a lens system 33 (indicated in dashed lines in the FIGS. 1 and 3) could be used for irradiating the liquid drop 2 to be inspected with light of a light emitting device 17, such as an arc lamp, a light emitting diode (LED), and a laser diode (that is a powerful LED with a defined wavelength). Thus, the optical measuring apparatus 1 preferably comprises a lens system 33 that is configured for defining a particular optical path of the light penetrating the liquid drop 2. In consequence, also the light arriving from the liquid drop 2 and that is to be guided to the detector 20 could be guided to the detector via a lens system 33 (not shown). The detector 20 of the optical measuring apparatus 1 preferably comprises a photodiode 20', a photomultiplier chip 20", a photomultiplier tube 20''', a CCD chip, or a CMOS chip 20'.

In order to know the actual length of the optical path for the light penetrating the liquid drop 2, the optical measuring apparatus 1 preferably comprises an imaging chip 32 that is configured for detecting an actual optical pathlength of the light penetrating the liquid drop 2. Such detection can be achieved by positioning the imaging chip 32 on a third optical axis 35 perpendicular to the first optical axis 14. The imaging chip 32 is extending parallel to the first optical axis 14 and at a right angle to the perpendicular third optical axis 35 (see FIG. 5). Preferably, the liquid drop 2 is irradiated with the light of a second light source 37 and a collimating lens is used to achieve proper projection 36 of the drop shape (see FIGS. 5, 7 and 8).

The FIG. 2 shows a vertical cross section through a liquid handling tip 4 holding at its liquid handling orifice 6 a suspended liquid drop 2 in a position between a light source 8 and a detector 10 of an optical measuring apparatus 1 according to a second embodiment. For working with this second embodiment, the same liquid handling system 3 as in the first embodiment can be used. Here, the light source 8 comprises an arc lamp 17' that is enclosed in a preferably well ventilated box equipped with a slit or pinhole 18"" through which the irradiation light 9 can exit the box. Preferably within this ventilated box, a lens 18" is placed between the arc lamp 17' and the slit or pinhole 18"". In the path of the irradiation light 9, a retractable (see double arrow) optical filter 18''' is placed. This optical filter 18''' can be a single optical filter or a series of optical filters (not shown) in each case preferably assembled on a filter slide or on a filter wheel. This optical filter 18''' provides for selecting a particular wavelength of the irradiation light 9 for irradiating the sample in the liquid drop 2. In addition, a monochromator can be used for selecting certain wavelengths (not shown). In agreement with the invention, the filter 18''' does not touch the drop 2, leaving a free first air space 15 between its surface and the surface of the drop 2. Here, the detector comprises a photomultiplier tube 20''' that is operatively connected to the processor 13 and enclosed in a preferably well ventilated box equipped with a slit or pinhole 19"" (not visible here) through which the sample light 11 can enter the box. In the path of the emission or sample light 11, a retractable (see double arrow) optical filter 19''' is placed. This optical filter 19''' can be a single optical filter or a series of optical filters in each case preferably assembled on a filter slide or on a filter wheel. This optical filter 19''' provides for selecting a particular wavelength of the emission or sample light 11 for detecting the light arriving from the liquid drop 2. In agreement with the invention, the filter 19''' doesn't touch the drop 2, leaving a free second air space 16 between its surface and the surface of the drop 2.

The FIG. 3 shows a vertical cross section through a liquid handling tip 4 holding at its liquid handling orifice 6 a suspended liquid drop 2 in a position between a light source 8 and a detector 10 of an optical measuring apparatus 1 according to a third embodiment. This third embodiment is identical to the first embodiment of FIG. 1 with the exception that on the detection side of the liquid drop 2, different elements are mounted. Here, a beam splitter 21 is arranged on the first optical axis 14, the beam splitter 21 being separated from the liquid drop 2 by the second air space 16. The beam splitter 21 directs a part of the sample light 11 along a second optical axis 23 that preferably includes an angle of 90° with the first optical axis 14. The second optical axis 23 preferably is horizontal or vertical, thus enabling a projection of the liquid drop 2 to be projected onto the imaging chip 32 that is configured as a CCD or CMOS chip. Preferably, the diameter of the light beam emerging from the liquid drop 2 (that is estimated to be perfectly round) is measured. By knowing this diameter of the (converging or diverging) light beam at a given distance from the liquid handling axis 5 and by backward calculation, the diameter of the liquid drop 2 may be calculated due to the lens effect of the drop radius. In consequence, the length of the optical path of the excitation light through the sample can be estimated. Most of the sample light however preferably is penetrating the beam splitter 21 and reaching the detector via a lens 19" that is concentrating the sample light 11 on the light receiver 20 that preferably is configured as a photodiode 20', a photomultiplier chip 20", a photomultiplier tube 20''', a CCD chip, or a CMOS chip 20', which is operatively connected to the processor 13. Measurement signals 12 are provided to the processor 13 by the light receiver 20 as in the previous embodiments.

The FIG. 4 shows a vertical cross section through a liquid handling tip 4 holding at its liquid handling orifice 6 a suspended liquid drop 2 in a position between a light source 8 and a detector 10 of an optical measuring apparatus 1 according to a fourth embodiment. Like in the second embodiment of FIG. 2, the light emitting device 17 is located in a box, from which the irradiation light 9 exits through an opening. Within the box for the light source 8, there also is a lens 18" for collimating the beam of the irradiation light 9 in the direction of the first optical axis 14, on which a beam splitter 21 in form of a dichroic mirror is located. This beam splitter 21 is configured to direct the irradiation light 9 through to the lens 19" that is concentrically arranged on the first optical axis 14 and between the beam splitter 21 and the liquid drop 2. The lens 19" concentrates the beam of irradiation light 9 to an entrance/exit surface of an optic fiber or fiber bundle 19' that is placed in the wall of a shield 24. Use of an optic fiber or fiber bundle 19' is optional however; instead, a simple slit or aperture will do.

The shield 24 encloses a part of the liquid handling tip 4 of the liquid handling system 3 in a way that an essentially closed detection space 25 around the liquid drop 2 that is hanging from the liquid handling tip 4 is established. Inside the detection space 25, but on the side of the liquid drop 2 that is opposite to the optic fiber or fiber bundle 19', a reflector 22 is mounted. Thus, a beam splitter 21 and a reflector 22 are arranged on the first optical axis 14, the beam splitter 21 being separated from the liquid drop 2 by the first air space 15 and the reflector 22 being separated from the liquid drop 2 by the second air space 16. By this configuration, the reflector 22 is directing back the sample light 11 to the liquid drop 2 thus doubling the pathlength for the light penetrating the liquid drop 2. In consequence, the optical measuring apparatus 1 comprises a shield 24 that encloses a detection space 25 and that comprises an opening 26. The opening 26 preferably is arranged to be penetrated by the liquid handling axis 5 and have a diameter 27 that allows friction free entering of the liquid handling tip 4 and positioning of the liquid drop 2 that is provided by the liquid handling system 3 and that is suspended at the liquid handling orifice 6 of the liquid handling tip 4 of the liquid handling system 3 in a position where the liquid drop 2 is penetrated by the first optical axis 14. Preferably in order to achieve a stable and defined position of the liquid drop 2 for inspection, the liquid handling tip 4 acts upon a cone or other surface. Less preferred is that the liquid handling tip 4 abuts a circular contact, and least preferred is a free positioning of the liquid handling tip 4 by a liquid handling robot that carries the liquid handling tip 4. The shield 24 preferably comprises at least one of a humidifying source 28 for controlling the humidity of the gas atmosphere of the detection space 25 inside the shield 24 and/or a temperature regulation source 29 for controlling the temperature of the gas atmosphere of the detection space 25 inside the shield 24.

The beam splitter 21 is arranged here on the first optical axis 14 at an oblique angle α to the first optical axis 14 and defines a second optical axis 23 that extends at an angle β to the first optical axis 14. Here, the light source 8 is arranged on the first optical axis 14 and the detector 10 (preferably in the form of a photodiode 20', a photomultiplier chip 20", a photomultiplier tube 20''', a CCD chip, or a CMOS chip 20') is located on the second optical axis 23. Between the beam splitter 21, which is configured to act as a mirror for the sample light 11 and to direct it to the detector 10, and the detector 10 an other lens 19" is located for concentrating the sample light 11 on the surface of the photodiode 20', photomultiplier chip 20", photomultiplier tube 20''', CCD chip, or CMOS chip 20'. Alternatively, the place of the light source 8 can be exchanged with the place of the detector 10; thus the detector 10 lays on the first optical axis 14 and the light source 8 lays on the second optical axis 23. In this case, the beam splitter 21 is configured to deflect the irradiation light 9 to the liquid drop 2 and to let pass the sample light 11 parallel to the first optical axis 14 and onto the photodiode 20', photomultiplier chip 20", photomultiplier tube 20''', CCD chip, or CMOS chip 20' of the detector 10.

The FIG. 5 shows a horizontal projection of the optical measuring apparatus 1 according to a fifth embodiment comprising a light source 8 and a detector 10, and of the liquid handling system 3 providing a liquid drop 2 suspended from the liquid handling orifice 6 of a liquid handling tip 4 and positioned in between the light source 8 and the detector 10. Here, the essentially spherical liquid drop 2 is placed so that the horizontal first optical axis 14 is penetrating the liquid drop 2 in its center; thus, the optical path of the light through the liquid drop 2 is maximal. Coaxially arranged with the first optical axis 14 are two lens systems 33, one for the irradiation light 9 and one for the sample light 11. A particular first wavelength of the irradiation light 9 is selected with a filter 18''' placed in front of the light source 8 and a particular second wavelength of the sample light 11 is selected with a filter 19''' placed in front of the detector 10.

The light emitting device 17 preferably is selected from a group that comprises an arc lamp 17', a laser, and a light emitting diode 17" (LED) and preferably is placed inside a ventilated box with a slit or pinhole 18''''. The light receiver 20 preferably is selected from a group that comprises a photodiode 20', a photomultiplier chip 20", a photomultiplier tube 20''', a CCD chip, or a CMOS chip 20' and preferably is placed inside a ventilated box with a slit or pinhole 19''''. Preferably, a lens 18" is placed between the light emitting device 17 and the slit or pinhole 18''''. In order to measure the length of the optical path of the light through the liquid drop 2, an imaging CCD or CMOS chip 32 is placed on a horizontal third optical axis 35 that runs perpendicular to the first optical axis 14. The light source 8, the detector 10, and the imaging chip 32 are operatively connected to the processor 13 for transferring measurement signals 12 and/or control signals. Preferably, the liquid drop 2 is irradiated with the light of a second light source 37 and a collimating lens is used to achieve proper projection 36 of the drop shape.

In general, the liquid drop 2 inspected acts like an optical lens and thus influences the optical path of the light. In consequence for optimal measurements, the drop size of preferably 1 to 2 mm in diameter should be adapted to a particular optical measurement system or alternatively, the optical measurement system should be adapted to a certain drop size. Mutual adaption of both, drop size and optical system is possible as well. Accordingly, any liquid handling system 3 can be used when working with the optical measuring apparatus 1. Such a liquid handling system 3 can be, on the high end, a robotic sample processor (RSP) like the already mentioned Freedom EVO® robotic workstation. In a much more simple approach, such a liquid handling system 3 can also be configured as hand pipette as long as the hand pipette is able to repeatedly provide defined drop volumes. Apparently, any liquid handling system 3 situated in its complexity between theses two extremes can be utilized for working in combination with the optical measuring apparatus 1 of the present invention.

Preferably, the liquid handling system 3 comprises a pump 39 that is controlled by a central processor 44 of the liquid handling system 3. The pump 39 is operatively connected to the liquid handling tip 4 via a pressure line 40 and a central processor 44 of the liquid handling system 3 is controlled by the processor 13 of the optical measuring apparatus 1. Thus, the pump 39 in effective combination with the processor 13 of the optical measuring apparatus 1 and with the central processor 44 of the liquid handling system 3 is a means for the adaption of the size of the liquid drop 2 with respect to the first and second optical elements 18,19 or with respect to at least one optical element 18,19 of the optics system 43. Moreover, the relative position of the liquid drop 2 with respect to the optics system 43 of the optical measuring apparatus 1, i.e. the first and second optical elements 18,19 of the optics system 43, can be mutually adapted as well. For coarse mutual positioning of liquid drop 2 and optics system 43, a robot arm 45 of the liquid handling system 3, to which robot arm 45 the liquid handling tip 4 is attached, can be utilized. Preferably, the robot arm 45 is configured to be controlled by the central processor 44 of the liquid handling system 3 and to be moved in one or more directions of a coordinate system. This coordinate system can be a Cartesian or any other coordinate system, so that robot arm 45 may be moved in a defined way in one or more directions of the respective coordinate system. Preferably, the robot arm 45 is accomplished in effective combination with the processor 13 of the optical measuring apparatus 1 and with the central processor 44 of the liquid handling system (3) and thus, the robot arm 45 is a means for the mutual adaption of the position of the liquid drop 2 with respect to the first and second optical elements 18,19 or with respect to at least one optical element 18,19 of the optics system 43.

Preferably in order to fine-tune the mutual position adaption of the liquid drop 2 with respect to the optics system 43, the liquid handling tip 4 is attached to the robot arm 45 of the liquid handling system 3 by a X/Y/Z drive 46 that is controlled by the central processor 44 of the liquid handling system 3 and that is configured for fine-tuning. Preferably the X/Y/Z drive 46 is based on piezo elements.

Alternatively or in combination with the already described means for the mutual adaption of the position of the liquid drop 2 with respect to the first and second optical elements 18,19 of the optics system 43, the light source 8 and the first optical elements 18 may be supported by a first dedicated X/Y/Z drive 47, and the detector 10 and the second optical elements 19 may be supported by a second dedicated X/Y/Z drive 48, the first and second dedicated X/Y/Z drives 47,48 being configured for fine-tuning the position adaption of the optics system 43 with respect to the liquid drop 2.

The FIG. 6A shows a horizontal projection of the situation of the liquid drop 2 to be investigated, with indicated preferred ranges for fluorescence or luminescence detection. It is highly preferred that the detector 42 for detecting fluorescence or luminescence emitted by the sample in the liquid drop 2 (i.e. the sample light) is not placed coaxial with the light source 8 and the droplet 2. If a fluorescence detector 42 is placed in a horizontal plane together with the light source 8, the droplet 2, and the first optical axis 14 that links these two, it is preferred to locate the fluorescence detector 42 in sectors on the side of the first optical axis 14 (indicated with double arrows) in order to prevent excitation or irradiation light 9 reaching the detector 42. In consequence, the second optical axis 23 that links the drop 2 with the detector 42 is orientated at an appropriate angle with respect to the first optical axis 14. The light source 8, the drop 2, and the fluorescence detector 42 could as well be placed on two or three different height levels, one such example is depicted in FIG. 6B.

The FIG. 6B shows a vertical section view of the situation of the liquid drop 2 to be investigated, with indicated preferred range for fluorescence or luminescence detection. A fluorescence detector 42 is placed on a lower level than the light source 8, the droplet 2, and the first optical axis 14 that links these two. Preferably, the fluorescence detector 42 is located in the sector below the first optical axis 14 (indicated with double arrow) in order to prevent excitation or irradiation light 9 reaching the detector 42. In consequence, the second optical axis 23 that links the drop 2 with the detector 42 is orientated at an appropriate angle with respect to the first optical axis 14.

It goes without saying that combinations of the detector placing as shown in the FIGS. 6A and 6B are possible too. Possible placements of a luminescence detector 42 may be chosen accordingly; however, as there usually is no excitation light, the luminescence detector may be placed even on the same optical axis as the (this time switched off) light source 8 and the drop 2.

The FIG. 7 shows a horizontal projection of the optical measuring apparatus 1 according to a sixth embodiment comprising a light source 8 and a detector 10. For adapting the drop size to the particular optical measurement system, the liquid handling system provides a pump 39 to vary the size of the liquid drop 2 suspended from the orifice 6 of a liquid handling tip 4 and positioned in between the light source 8 and the detector 10. The FIG. 7 in many aspects resembles the fifth embodiment as shown in FIG. 5, but depicts the setup actually used for testing the current invention. Again, the essentially spherical liquid drop 2 is placed so that the horizontal first optical axis 14 is penetrating the liquid drop 2 in its center; thus, the optical path of the light through the liquid drop 2 is maximal. The light emitting device 17 is a Deuterium Lamp. Coaxially arranged with the first optical axis 14 are two lenses 18" and 19" (quartz lenses G312412000 of Qioptiq LINOS, Inc., Munich, Germany), one for the irradiation light 9 and one for the sample light 11. Between the liquid drop 2 and the lens 19", an intermediate lens system 41 (consisting of a lens DCX 49254 and DCX 49255 of Edmund Optics Ltd., York, United Kingdom) is coaxially placed. The detector 10 is a CCD camera. Similar as in FIG. 5, the drop 2 is irradiated with the light of a second light source 37 and a collimating lens 38 is used to achieve proper projection 36 of the drop shape on the sensor 32 of a CCD camera. In order to measure the length of the optical path of the light through the liquid drop 2, an imaging chip 32 of a CCD camera is placed on a horizontal third optical axis 35 that runs perpendicular to the first optical axis 14. The light source 8, the detector 10, and the imaging chip 32 of the CCD camera are operatively connected to the processor 13 for transferring measurement signals 12 and/or control signals.

In this sixth embodiment of the inventive optical measuring apparatus 1, a pump 39 is provided and operatively connected to the liquid handling tip 4 by a pressure line 40. The pump 39 is also connected with the processor 13 and the processor is connected with imaging CCD 32 sensor. This arrangement provides a closed-loop control for adjusting the size of the liquid drop 2. In detail first, a liquid drop 2 is produced at the liquid handling orifice 6 of the liquid handling tip 4. Then, in a number of iteration cycles (until the desired drop size and position is reached) the following steps are repeatedly carried out:

a) an image of the liquid drop 2 is recorded, using the second light source 37 and the imaging chip 32;
b) by processing this image, the actual size of the liquid drop is calculated; and
c1) the drop size and drop position is corrected according to the result of step b), or
c2) the drop size and optics position is corrected according to the result of step b).

Changing drop size may be effected by appropriately changing the pressure in the pressure line 40 with the pump 39, wherein lowering the pressure would reduce and raising the pressure would enlarge the size of the liquid drop 2. A liquid drop 2 with a preferred size has a diameter of about 1 to 2 mm.

Changing drop position may be effected by moving the liquid handling tip 4 (preferably attached to a robot arm of the liquid handling system 3) in one or more directions of the axes of a three dimensional Cartesian or any other coordinate system. The drive of the robot arm that carries the liquid handling tip 4 can be used for coarse movements. For fine-tuning movements, a dedicated X/Y/Z drive that is located between the robot arm and the liquid handling tip 4 may be moved; preferably the dedicated X/Y/Z drive is based on piezo elements.

Changing optics position may be effected by moving the light source 8, its first optical elements 18 as well as the detector 10 with its second optical elements 19 with a dedicated X/Y/Z drive; preferably the dedicated X/Y/Z drive is based on piezo elements.

All drives for the necessary movements described here as well as the pump 39 are controlled by the processor 13 and thus all necessary changes may me carried out automatically. Following to the necessary iteration cycles, absorbance of the irradiation light 9 of the light source 8 is measured using the optic system and detector 10. Simultaneously or alternately, fluorescence or luminescence of the sample in the liquid drop 2 can be measured too.

The FIG. 8 shows a horizontal projection of the optical measuring apparatus 1 according to a seventh embodiment comprising a light source 8 and a detector 10 and already described elements of the fifth and sixth embodiments. Different to the embodiments described so far, this seventh embodiment comprises a fluorescence or luminescence detector 42 for measuring fluorescence or luminescence emitted by the sample in the liquid drop 2 suspended from the orifice 6 of a liquid handling tip 4 and positioned in between the light source 8 and the detector 42. In order to enable fluorescence or luminescence measurements, a beam splitter 21 is located at an oblique angle on the third optical axis 35. This beam splitter 21 is configured to deflect fluorescence or luminescence light emitted by the sample and arriving from the liquid drop 2 into the fluorescence or luminescence detector 42 that is preferably equipped with a photomultiplier chip 20". By the arrangement shown in FIG. 8, it is made sure that only fluorescent or luminescence light from the sample and no light of the excitation source (the light emitting device 17) are allowed to enter the fluorescence or luminescence detector 42 and to reach the photomultiplier chip 20". In order to achieve this goal, the optical measuring apparatus 1 comprises a fluorescence or luminescence detector 42 that is located beyond the first optical axis 14 and third optical axis 35. Only for measuring the fluorescence or luminescence signal, instead of a beam splitter 21 a simple mirror could be used (not shown) or alternatively, the fluorescence or luminescence detector 42 with the photomultiplier chip 20" could be located on the third optical axis 35 (not shown either). In all of these simplified embodiments that are only dedicated to an optical measuring apparatus 1 for fluorescence or luminescence measurements, the second light source 37 and the imaging chip 32 could be dispensed with. If the detector 10 should be used simultaneously to fluorescence or luminescence measurements, determination of the drop size could be carried out by calculations that are based on the Beer Lambert Law (see below).

In any case, the light source 8 and the liquid drop 2 define the first optical axis 14 that extends essentially perpendicular to the liquid handling axis 5. It is however left to the skilled person whether a detector 10 (i.e. one of a photodiode 20', a photomultiplier chip 20", a photomultiplier tube 20'", a CCD chip, or a CMOS chip 20') is to be placed on this first optical axis 14 as well (see FIGS. 1, 2, 3, 5, 7, and 8) or whether the detector 10 is to be placed on a different, second optical axis 23 (see FIGS. 4 and 6A, 6B).

It is expressly pointed out here, that all different devices and elements shown and/or described herein can be rearranged and exchanged according to the actual needs of a skilled person without departing from the gist of the present invention, as long as the liquid drop 2 is not physically touched by any light emitting device 17 or light receiver 20.

The optical measuring apparatus 1 of the present invention can be utilized for carrying out an optical measuring method of analyzing samples contained in liquid drops 2 that are provided by liquid handling systems 3. The analyzing method according to the present invention comprises the steps of:

(a) providing a liquid handling system 3 which comprises at least one liquid handling tip 4 with a liquid handling axis 5 and with a liquid handling orifice 6 at a distal end 7 of the liquid handling tip 4, the liquid handling axis 5 extending inside the liquid handling tip 4 and penetrating the liquid handling orifice 6;

(b) providing a liquid drop 2 that is suspended at the liquid handling orifice 6 of the liquid handling tip 4 of the liquid handling system 3 in a position where the liquid drop 2 is penetrated by a first optical axis 14 that extends essentially perpendicular to the liquid handling axis 5;

(c) providing an optical measuring apparatus 1 that comprises a light source 8, a detector 10, an optics system 43 with first optical elements 18 for transmitting irradiation light 9 from the light source 8 to the liquid drop 2 and with second optical elements 19 for transmitting sample light 11 from the liquid drop 2 to the detector 10 (see also FIGS. 6A and 6B); the irradiation source 8 and the liquid drop 2 defining the first optical axis 14 of the first optical elements 18 of the optics system 43, a first and second air space 15,16 separating the liquid drop 2 from the light source 8 and detector 10 and their associated first and second optical elements 18,19 that thus do not contact the liquid drop 2;

(d) irradiating the liquid drop 2 with irradiation light 9 originating from the light source 8;

(e) measuring sample light 11 arriving from the liquid drop 2 and providing measurement signals 12 with the detector 10; and (f) processing with a processor 13 that is operatively connected to the detector 10 the measurement signals 12 provided by the detector 10.

Optionally, a step (g) may be carried out in addition, wherein an amount of a sample to be delivered is adjusted, the adjustment being based on the result of the measurement that is provided by the previously carried out step (f).

Preferably, when carrying out the analyzing method according to the present invention, the size and position of the liquid drop 2 as well as the first and second optical elements 18,19 of the optics system 43 are already mutually adapted for achieving the highest signal/noise ratio. As an also preferred alternative, the analyzing method according to the present invention my comprise mutual adaption of the size and position of the liquid drop 2 with respect to the first and/or second optical elements 18,19 of the optics system 43 as described below.

According to the present invention, during analyzing the sample in the liquid drop 2, the liquid drop 2 only contacts the liquid handling tip 4 (in particular the liquid handling orifice 6) of the liquid handling system 3 and eventually some sample liquid volume 30 present inside the liquid handling tip 4. No other part of the liquid handling system 3 and no part of the optical measuring apparatus 1 of the present invention is physically touching the liquid drop 2 during analyzing the sample. Under this regime, the following process steps of the optical measuring method are carried out:

(i) aspirating from a sample source a volume of a liquid sample 30 with a liquid handling tip 4 of the liquid handling system 3;
(ii) moving the liquid handling tip 4 with the liquid sample 30 volume to the optical measuring apparatus 1, using the liquid handling system 3;
(iii) carrying out a controlled dispense action with the liquid handling system 3 and thereby creating a liquid drop 2 small enough to remain attached to the liquid handling orifice 6 of the liquid handling tip 4;
(iv) positioning the liquid handling tip 4 with the liquid drop 2 attached so that the liquid drop 2 is penetrated by a first optical axis 14 of the optical measuring apparatus 1; and
(v) mutually adjusting droplet size and optics system for optimizing measurement signals 12.

It is noted here that the steps (iii) and (iv) can be interchanged so that first the liquid handling tip 4 is placed at a defined position using a liquid handling robot of the liquid handling system 3, and then a controlled dispense action with the liquid handling system 3 is carried out thereby creating a liquid drop 2 small enough to remain attached to the liquid handling orifice 6 of the liquid handling tip 4. The optical property of interest of the sample contained in the liquid drop 2 preferably is selected from the group comprising absorbance, fluorescence, and luminescence. It is also noted here that the steps (iv) and (v) can be repeated for mutually optimizing the size of the liquid drop 2 and its position with respect to the optics system 43.

Consequently, the following steps preferably are carried out:
(vi) measuring optical properties of interest of the sample contained in the liquid drop 2;
(vii) re-aspirating the liquid drop 2 with the liquid handling system 3; and
(viii) dispensing at least a part of the volume of the liquid sample 30.

In order to optimize the relative spatial position of the liquid handling tip 4 with the liquid drop 2 and of the first optical axis 14 of the optical measuring apparatus 1, positioning of the liquid handling tip 4 with the liquid drop 2 attached (according to step (iv)) preferably is improved in that the measurement signals 12 provided with the detector 10 and received by the processor 13 are maximized through moving the liquid handling tip 4 into at least one of an X-, Y-, and Z-direction of a Cartesian coordinate system of the liquid handling system 3. It is especially preferred in this case that positioning the liquid handling tip 4 with the liquid drop 2 attached is improved in that a quadrant-style photo detector 31 (see FIG. 1) is utilized and the liquid handling tip 4 of the liquid handling system 3 is moved (if required) in an X-, Y-, and Z-direction of a Cartesian coordinate system until the measurement signal 12 of all four quadrants of the quadrant-style photo detector 31 are equalized.

It is particularly preferred that positioning the liquid handling tip 4 with the liquid drop 2 attached according to step (iv) is improved in that the liquid handling tip 4 is forced with a liquid handling robot of the liquid handling system 3 to act upon a surface 34, thus positioning the attached liquid drop 2 at a site that previously had been approved for providing best measurement results.

It is also preferred that with the liquid drop 2 attached according to step (iv), the liquid drop 2 is modified in drop shape and/or position in order to optimize the measurement signals 12 provided with the detector 10. Mutual adjustment of droplet size and optics system can be achieved by adopting the drop size to an existing optical system, i.e. to control the drop size with the pump 39 in order to achieve a predefined optimal drop size. Alternatively, the optical system can be adapted to an actual (unknown) drop size using e.g. at least one zoom lens 18" or 19" according to the knowledge of a person skilled in optics. It is also possible to utilize variable optics (with e.g. zoom lenses) and to simultaneously modify the drop size with a pump 39.

For determining the actual optical pathlength of the light penetrating the liquid drop 2, different methods can be applied:

1. A beam splitter 21 is placed between the liquid drop 2 and the detector 10 of the optical measuring apparatus 1 (see FIG. 3), the beam splitter 21 directing a part of the sample light 11 to an imaging CCD or CMOS chip 32, and the shape of the liquid drop 2 is imaged using the signals detected by the imaging CCD or CMOS chip 32 (see FIG. 3). This method is limited to liquid drops 2 that exhibit essentially spherical shape with a horizontal drop diameter that is equal in all directions.
2. An imaging CCD or CMOS chip 32 is placed on a third, horizontal optical axis 35 that runs perpendicular to the first optical axis 14 (see FIG. 5). Preferably, a collimating lens 38 is placed on the third optical axis 35 between the liquid drop 2 and the imaging chip 32; thus, a defined projection 36 of the liquid drop 2 is rendered on the surface of the imaging chip 32. The actual length of the optical path of the light penetrating the liquid drop 2 is measured on the image created with the imaging CCD or CMOS chip 32. This method has the advantage that indeed the actual pathlength is measured, independent from the actual symmetry or asymmetry of the liquid drop 2.
3. If a known solvent is used with the sample to be investigated, the optimal drop size can be determined and the pressure in the pipette tip (the liquid handling tip 4) can be recorded for this solvent and optimal drop size. By reproducing the pressure in the liquid handling tip 4, the drop size is reproduced. In order to measure the pressure inside the liquid handling tip 4, the liquid handling system has to be equipped with an appropriate pressure transducer and measurement. This method has the advantage that no imaging and further measurement has to be carried out. However, this method is limited to liquid drops 2 that exhibit essentially spherical shape with a horizontal drop diameter that is equal in all directions. It is to be noted however that the drop size may also depend on the drop temperature and liquid properties (e.g. surface tension, viscosity, saturation vapor pressure etc.). This method is recommended for a drop size of less than 2 mm in diameter, because it has been found that for such small liquid drops the pressure changes with the drop size.
4. The optical pathlength of the light penetrating the liquid drop 2 is preferably determined by:
   measuring a first light signal resulting from transmission of light, having a first predetermined wavelength, and measuring a second light signal resulting from transmission of light, having a second predetermined wavelength, and determining the optical pathlength of the sample from a predetermined relationship between the first and second light signal, and the optical pathlength of the solvent, wherein the first and second wavelength are in a near-infrared region of an electromagnetic spectrum of from 750 nanometers to 2500 nanometers wavelength.

5. The optical pathlength (L) of the light penetrating the liquid drop 2 is calculated according to the formula:

$$L = \frac{A_1 - A_2}{C(\varepsilon_1 - \varepsilon_2)}. \tag{1}$$

Wherein:
$A_1$ is a first absorption value resulting from the first light signal, $A_2$ is a second absorption value, resulting from the second light signal, and
$C$ ($\varepsilon_1$-$\varepsilon_2$) is predetermined or determined from the absorption at said first and second wavelengths of a reference cuvette containing a solvent sample of predetermined optical pathlength.

6. The optical pathlength (L) of the light penetrating the liquid drop 2 is calculated according to the formula:

$$L = \frac{A}{\varepsilon \cdot C}. \tag{2}$$

Wherein:
A is the absorbance value resulting from the light signal $\lambda_1$,
$\varepsilon$ is the extinction coefficient of the substance at $\lambda_1$, and
C is the molecular concentration of the substance in the drop.

The methods 4 to 6 have the advantage that indeed the actual optical pathlength of the light penetrating the liquid drop 2 is measured or calculated and no imaging or further measurement has to be carried out. Independent of the drop size and geometry, these methods can be carried out in an automated way utilizing appropriate software that is activated in the processor 13.

If the optical measuring apparatus 1 comprises a shield 24 that encloses a detection space 25 and that comprises an opening 26 with a diameter 27, and if the liquid handling tip 4 is entered trough the opening 26, and after positioning the liquid handling tip 4 with the liquid drop 2 attached according to step (iv), the temperature and/or humidity of the gas atmosphere in the detection space 25 inside the shield 24 are controlled by a temperature regulation source 29 and/or a humidifying source 28 (see FIG. 4).

According to the actual needs of a person working with the optical measuring apparatus 1 according to the present invention and with an adequate liquid handling system 3, dispensing at least a part of the volume of the liquid sample 30 preferably is carried out according to step (vii) as follows:
the entire volume of the liquid sample 30 is dispensed back into the sample source, or
parts of the volume of the liquid sample 30 are dispensed into at least one reaction container and the residual volume of the liquid sample 30 is dispensed back into the sample source or into a waste sink, or
the entire volume of the liquid sample 30 is dispensed into at least one reaction container.

According to an especially preferred use of the optical measuring apparatus 1 according to the present invention and according to a particularly preferred application of the optical measuring method, dispensing at least a part of the volume of the liquid sample 30 is carried out according to step (vii) as follows:
the optical pathlength of the light penetrating the liquid drop 2 is determined or calculated utilizing the Beer Lambert Law;
the concentration of the sample 30 in the liquid drop 2 is calculated according to the Beer Lambert Law;
a certain mass of the sample 30 is determined according to the concentration in the liquid drop 2;
the certain mass of the sample 30 is dispensed.

As known in molecular biology, reactions or assays that use nucleic acids often require particular amounts and purity for optimum performance. In consequence, quantitation of nucleic acids is commonly performed to determine the average concentrations of DNA or RNA present in a mixture, as well as their purity. Nucleic acids absorb ultraviolet light in a specific pattern. In a spectrophotometer, a sample is exposed to ultraviolet light at 260 nm, and a photodetector measures the light that passes through the sample. The more light absorbed by the sample, the higher the nucleic acid concentration in the sample. Using the Beer Lambert Law it is possible to relate the amount of light absorbed to the concentration of the absorbing molecule.

The Beer Lambert Law:

$$D = \log_{10}(I_0/I) = \varepsilon CL \tag{2}$$

Wherein:
D=optical density, absorbance
$I_0$=intensity of incident light at wavelength A
I=intensity of light after passing through absorption cell
C=concentration of the absorbing material (molar)
L=length of absorption path
$\varepsilon(\lambda)$=extinction coefficient It is noted that the validity of this relation is generally satisfactory if the radiation is monochromatic, if the concentrations of absorbing material are low, and if there are no significant molecular interactions, such as association, dissociation or structural changes for different concentrations.

At a wavelength of 260 nm, the average extinction coefficient for double-stranded DNA is 0.020 $(\mu g/ml)^{-1}$ $cm^{-1}$, for single-stranded DNA it is 0.027 $(\mu g/ml)^{-1}$ $cm^{-1}$, for single-stranded RNA it is 0.025 $(\mu g/ml)^{-1}$ cm' and for short single-stranded oligonucleotides it is dependent on the length and base composition. Thus, an optical density (or "OD") of 1 corresponds to a concentration of 50 µg/ml for double-stranded DNA. This method of calculation is valid for up to an OD of at least 2. A more accurate extinction coefficient may be needed for oligonucleotides; these can be predicted using the nearest-neighbor model.

It is common for nucleic acid samples to be contaminated with other molecules (i.e. proteins, organic compounds, etc.). The ratio of the absorbance at 260 and 280 nm ($A_{260/280}$) is used to assess the purity of nucleic acids. For pure DNA, $A_{260/280}$ is ~1.8 and for pure RNA, $A_{260/280}$ is ~2.

The ratio of absorptions at 260 nm vs. 280 nm is commonly used to assess DNA contamination of protein solutions, since proteins (in particular, the aromatic amino acids) absorb light at 280 nm. The reverse, however, is not true: it takes a relatively large amount of protein contamination to significantly affect the 260:280 ratio in a nucleic acid solution. This difference is due to the much higher extinction coefficient nucleic acids have at 260 nm and 280 nm, compared to that of proteins. Because of this, even for relatively high concentrations of protein, the protein contributes relatively little to the 260 and 280 absorbance. While the protein contamination cannot be reliably assessed with a 260:280 ratio, this also means that it contributes little error to DNA quantity estimation.

It is thus preferred to expose a sample to ultraviolet light at 260 nm and at 280 nm, to measure the light that passes through the sample with a photo-detector, and to assess the purity of nucleic acids using the Beer Lambert Law on the ratio of the absorbance at 260 and 280 nm ($A_{260/280}$). Such quantitation can be performed using each one of the disclosed embodiments of the optical measuring apparatus 1.

The FIG. 9 shows a comparison of absorbance spectra (unprocessed raw signals) of a buffer drop with DNA and a buffer drop without DNA as captured with the optical measuring apparatus 1 of the present invention. The optical system is designed for a drop size of 1.76 mm and a central irradiation of the liquid drop 2. The drop size and position was recorded with a CCD camera 32 on axis 35. The processor 13 uses the information from the CCD camera 32 to compare the actual size and position to the target values. With the liquid handling system 3, the processor 13 regulates the position and size. When target values are reached, the light source 8 is switched on and a spectrum is recorded with the detector 10 (the light receiver 20). There, the signal (intensity of the transmitted light in counts) is drawn against the wavelength of the light used for penetrating the sample in the liquid drop 2. At wavelengths higher than about 300 nm, there is essentially no difference between the two measurements. However, in the range between 210 and 300 nm, the liquid drop 2 with the DNA sample (500 ng/ml DNA in 1.76 mm buffer drop) shows a much higher absorbance than the liquid drop 2 without DNA sample (1.76 mm buffer drop only).

The FIG. 10 shows a comparison of absorbance spectra (processed raw signals) of the same DNA sample in buffer as captured with the optical measuring apparatus of the present invention (i.e. using the sixth embodiment of FIG. 7 as herein disclosed) or captured with a commercially available spectrometer. In order to compare a raw signal of the FIG. 9 with a result obtained with a commercial spectrometer, the raw signal was post processed by correcting for the dark current of the sensor and the signal level adjusted at 315 nm. Good correlation of the two graphs is noted at a wavelength between 230 nm and 315 nm. Only minor differences are visible which can be assigned a possible difference in wavelength calibration. It is therefore concluded that absorption at 260 nm and 280 nm can be credibly measured with the optical measuring apparatus 1 of the present invention. Accordingly, the ratio of absorptions at 260 nm vs. 280 nm can be credibly determined using the optical measuring apparatus 1 of the present invention.

The same or similar elements in the different Figures are indicated with the same or similar reference numbers. Therefore, these indications and the related elements in the drawings entirely disclose all these elements to a person of skill, even when not every detail is discussed in each case.

One or more liquid handling systems 3 can be used in combination with one optical measuring apparatus 1 of the present invention. A single liquid handling system 3 can be equipped with one or more measuring apparatuses 1 according to the present invention.

| Reference numbers | |
|---|---|
| 1 | optical measuring apparatus |
| 2 | liquid drop |
| 3 | liquid handling system |
| 4 | liquid handling tip |
| 5 | liquid handling axis |
| 6 | liquid handling orifice |
| 7 | distal end of 4 |
| 8 | light source |
| 9 | irradiation light |
| 10 | detector |
| 11 | sample light |
| 12 | measurement signals |
| 13 | processor |
| 14 | first optical axis |
| 15 | first air space |
| 16 | second air space |
| 17 | light emitting device |
| 17' | arc lamp |
| 17" | light emitting diode (LED) |
| 18 | first optical element |
| 18' | optic fiber or fiber bundle |
| 18" | lens |
| 18''' | filter |
| 18'''' | slit or pinhole |
| 19 | second optical element |
| 19' | optic fiber or fiber bundle |
| 19" | lens |
| 19''' | filter |
| 19'''' | slit or pinhole |
| 20 | light receiver |
| 20' | photodiode, CCD chip, CMOS chip |
| 20" | photomultiplier chip |
| 20''' | photomultiplier tube |
| 21 | beam splitter |
| 22 | reflector |
| 23 | second optical axis |
| 24 | shield |
| 25 | detection space |
| 26 | opening |
| 27 | diameter of 26 |
| 28 | humidifying source |
| 29 | temperature regulation source |
| 30 | liquid sample |
| 31 | quadrant-style photo detector |
| 32 | imaging CCD or CMOS chip |
| 33 | lens system |
| 34 | cone surface |
| 35 | third optical axis |
| 36 | projection of liquid drop on 32 |
| 37 | second light source |
| 38 | collimating lens |
| 39 | pump |
| 40 | pressure line |
| 41 | intermediate lens system |
| 42 | fluorescence or luminescence detector |
| 43 | optics system |
| 44 | central processor of 3 |
| 45 | robot arm of 3 |
| 46 | X/Y/Z drive |
| 47 | first dedicated X/Y/Z drive |
| 48 | second dedicated X/Y/Z drive |

What is claimed is:

1. An optical measuring apparatus (1) configured for the analysis of samples contained in liquid drops (2) that are provided by a liquid handling system (3), the optical measuring apparatus (1) comprising:
   a) a liquid handling system (3) with at least one liquid handling tip (4) that comprises a liquid handling axis (5) and a liquid handling orifice (6) at a distal end (7), the liquid handling axis (5) extending inside the liquid handling tip (4) and penetrating the liquid handling orifice (6); the liquid handling system (3) comprising a pump (39) that is controlled by a central processor (44)

of the liquid handling system (3), the pump (39) being operatively connected to the liquid handling tip (4) via a pressure line (4);

b) a light source (8) configured for providing irradiation light (9) for irradiating a liquid drop (2) of a liquid sample (30) provided by the liquid handling system (3); the light source (8) and the liquid drop (2) defining a first optical axis (14) of first optical elements (18) of an optics system (43) that extends essentially perpendicular to the liquid handling axis (5), the liquid drop (2) provided by the liquid handling system (3) being suspended at the liquid handling orifice (6) of the liquid handling tip (4) in a position where the liquid drop is penetrated by the first optical axis (14);

c) a detector (10) configured for measuring sample light (11) arriving from said liquid drop (2) and for providing measurement signals (12) that represent the measured sample light (11);

d) an optics system (43) with first optical elements (18) for transmitting the irradiation light (9); and e) a processor (13) connected to the detector (10) and configured to accept and process the measurement signals (12) provided by the detector (10);

the liquid drop (2) being physically separated from the optics system (43) of the optical measuring apparatus (1) and being physically touched only by the liquid handling tip (4) of the liquid handling system (3) and the liquid sample (30) inside the liquid handling tip (4), the light source (8) with the first optical elements (18) being thus separated from the liquid drop (2) by a first air space (15) and the detector (10) being thus separated from the liquid drop (2) by a second air space (16), wherein the optics system (43) comprises second optical elements (19) for transmitting the sample light (11) from the liquid drop (2) to the detector (10), the second optical elements (19) being separated from the liquid drop (2) by a second air space (16), and wherein the optical measuring apparatus (1) further comprises a dedicated X/Y/Z drive controlled by the processor (13) and configured for moving the light source (8), its first optical elements (18) as well as the detector (10) with its second optical elements (19).

2. The optical measuring apparatus (1) of claim 1, wherein the dedicated X/Y/Z drive comprises a first dedicated X/Y/Z drive (47) and a second dedicated X/Y/Z drive (48), both dedicated X/Y/Z drives (47,48) being based on piezo elements and configured for fine-tuning a position adaption of the optics system (43) with respect to the liquid drop (2).

3. The optical measuring apparatus (1) of claim 1, wherein the detector (10) with the second optical elements (19) of the optical measuring apparatus (1) is located on the first optical axis (14) or on a second optical axis (23).

4. The optical measuring apparatus (1) of claim 3, wherein the optical measuring apparatus (1) comprises an imaging chip (32) that is configured for detecting an actual optical pathlength of the light penetrating the liquid drop (2) or for controlling the size and position of the liquid drop (2).

5. The optical measuring apparatus (1) of claim 4, wherein the optical measuring apparatus (1) comprises a second light source (37) and a collimating lens (38) for imaging the size and/or position of the liquid drop (2), the second light source (37), collimating lens (38) and imaging chip (32) being located on a third optical axis (35).

6. The optical measuring apparatus (1) of claim 5, wherein the optical measuring apparatus (1) comprises a second detector (42) that is located outside of the first optical axis (14), the second detector (42) being selected from a fluorescence detector and a luminescence detector.

7. The optical measuring apparatus (1) of claim 1, wherein the processor (13) of the optical measuring apparatus (1) comprises an algorithm that is configured for calculating an actual optical pathlength of the light penetrating the liquid drop (2).

8. The optical measuring apparatus (1) of claim 1, wherein a beam splitter (21) and a reflector (22) are arranged on the first optical axis (14), the beam splitter (21) being separated from the liquid drop (2) by the first air space (15) and the reflector (22) being separated from the liquid drop (2) by the second air space (16), the reflector (22) directing back the sample light (11) to the liquid drop (2) thus doubling a pathlength for the light penetrating the liquid drop (2).

9. The optical measuring apparatus (1) of claim 1, wherein the optical measuring apparatus (1) comprises a shield (24) that encloses a detection space (25) and that comprises an opening (26), the opening (26) being arranged to be penetrated by the liquid handling axis (5) and having a diameter (27) that allows friction free entering of the liquid handling tip (4) and positioning of the liquid drop (2) that is provided by the liquid handling system (3) and that is suspended at the liquid handling orifice (6) of the liquid handling tip (4) in a position where the liquid drop (2) is penetrated by the first optical axis (14).

10. The optical measuring apparatus (1) of claim 9, wherein the shield (24) comprises at least one of a humidifying source (28) for controlling humidity of a gas atmosphere of the detection space (25) inside the shield (24) and a temperature regulation source (29) for controlling the temperature of the gas atmosphere of the detection space (25) inside the shield (24).

11. The optical measuring apparatus (1) of claim 1, wherein the pump (39) in effective combination with the processor (13) of the optical measuring apparatus (1) and with the central processor (44) of the liquid handling system (3) is a means for adapting the size of the liquid drop (2) with respect to at least one optical element (18,19) of the optics system (43).

12. The optical measuring apparatus (1) of claim 11, wherein the liquid handling system (3) comprises a robot arm (45) that is controlled by the central processor (44) of the liquid handling system (3), the liquid handling tip (4) being attached to the robot arm (45), and the robot arm (45) being configured to be moved in one or more directions of a coordinate system, and wherein the robot arm (45) in effective combination with the processor (13) of the optical measuring apparatus (1) and with the central processor (44) of the liquid handling system (3) is a means for adapting the position of the liquid drop (2) with respect to the first and/or second optical elements (18,19) of the optics system (43).

13. The optical measuring apparatus (1) of claim 12, wherein the liquid handling tip (4) is attached to the robot arm (45) of the liquid handling system (3) by a X/Y/Z drive (46) that is controlled by the central processor

(44) of the liquid handling system (3) and that is configured for fine-tuning the position adaption of the liquid drop (2) with respect to the optics system (43).

14. Liquid handling system (3), comprising an optical measuring apparatus (1) according to claim 1, which liquid handling system (3) comprises at least one liquid handling tip (4) that comprises a liquid handling axis (5) and a liquid handling orifice (6) at a distal end (7), the liquid handling axis (5) extending inside the liquid handling tip (4) and penetrating the liquid handling orifice (6), wherein the liquid handling system (3) comprises a central processor (44) and a pump (39), which pump (39) is operatively connected to the liquid handling tip (4) via a pressure line (40), and which pump (39) is controlled by the central processor (44) of the liquid handling system (3); the processor (13) of the optical measuring apparatus (1) being operatively linked to the central processor (44), and wherein the pump (39) in effective combination with the processor (13) of the optical measuring apparatus (1) and with the central processor (44) of the liquid handling system (3) is a means for adapting liquid drop (2) size with respect to at least one optical element (18,19) of the optics system (43).

15. An optical measuring method of analyzing samples contained in liquid drops (2) that are provided by liquid handling systems (3), wherein the method comprises the steps of:
(a) providing a liquid handling system (3) which comprises at least one liquid handling tip (4) with a liquid handling axis (5) and with a liquid handling orifice (6) at a distal end (7) of the liquid handling tip (4), the liquid handling axis (5) extending inside the liquid handling tip (4) and penetrating the liquid handling orifice (6); the liquid handling system (3) comprising a pump (39) that is controlled by a central processor (44) of the liquid handling system (3), the pump (39) being operatively connected to the liquid handling tip (4) via a pressure line (40);
(b) providing a liquid drop (2) that is suspended at the liquid handling orifice (6) of the liquid handling tip (4) of the liquid handling system (3) in a position where the liquid drop (2) is penetrated by a first optical axis (14) that extends essentially perpendicular to the liquid handling axis (5);
(c) providing an optical measuring apparatus (1) that comprises a processor (13) a light source (8), a detector (10), and an optics system (43) with first optical elements (18) for transmitting irradiation light (9) from the light source (8) to the liquid drop (2) and with second optical elements (19) for transmitting sample light (11) from the liquid drop (2) to the detector (10); the light source (8) and the liquid drop (2) defining the first optical axis (14) of the first optical elements (18) of the optics system (43); a first and second air space (15,16) separating the liquid drop (2) from the light source (8) and detector (10) and their associated first and second optical elements (18,19) that thus do not contact the liquid drop (2);
(d) irradiating the liquid drop (2) with irradiation light (9) originating from the light source (8);
(e) using at least one X/Y/Z drive controlled by the processor (13), moving at least one of the first optical elements (18) and the second optical elements (19) to align the liquid drop (2) and the optics system (43);
(f) measuring sample light (11) arriving at the detector (10) from the liquid drop (2) and providing measurement signals (12) with the detector (10); and (g) processing with the processor (13) that is operatively connected to the detector (10) the measurement signals (12) provided by the detector (10).

16. The optical measuring method of claim 15, further comprising:
(h) adjusting an amount of sample liquid to be delivered for producing the liquid drop (2) based on the measurement signals (12).

17. The optical measuring method of claim 15, which comprises the following steps:
(i) aspirating from a sample source a volume of a liquid sample (30) with a liquid handling tip (4) of the liquid handling system (3);
(ii) moving the liquid handling tip (4) with the liquid sample (30) volume to the optical measuring apparatus (1), using the liquid handling system (3);
(iii) carrying out a controlled dispense action with the liquid handling system (3) and thereby creating a liquid drop (2) small enough to remain attached to the liquid handling orifice (6) of the liquid handling tip (4);
(iv) positioning the liquid handling tip (4) with the liquid drop (2) attached so that the liquid drop (2) is penetrated by a first optical axis (14) of the optical measuring apparatus (1);
(v) mutually adjusting droplet size and optics system (43) for optimizing measurement signals (12); and optionally
(vi) repeating the steps (iv) an (v) for mutually optimizing the size of the liquid drop (2) and its position with respect to the optics system (43).

18. The optical measuring method of claim 17, further comprising the steps of:
(vii) measuring optical properties of interest of the sample contained in the liquid drop (2);
(viii) re-aspirating the liquid drop (2) with the liquid handling system (3); and
(ix) dispensing at least a part of the volume of the liquid sample (30).

19. The optical measuring method of claim 18,
wherein the optical property of interest of the sample contained in the liquid drop (2) is selected from the group comprising absorbance, fluorescence, and luminescence.

20. The optical measuring method of claim 18,
wherein dispensing at least a part of the volume of the liquid sample (30) is carried out according to step (ix) as follows:
the optical path length of the light penetrating the liquid drop (2) is determined or calculated utilizing the Beer Lambert Law;
the concentration of the sample (30) in the liquid drop (2) is calculated according to the Beer Lambert Law;
a certain mass of the sample (30) is determined according to the concentration in the liquid drop (2);
the certain mass of the sample (30) is dispensed.

21. The optical measuring method of claim 18,
wherein the liquid drop (2) comprises nucleic acids; and
wherein the liquid drop is exposed to ultraviolet light at 260 nm and at 280 nm, light that passes through the liquid drop (2) is measured with a photodetector, and purity of nucleic acids in the liquid drop (2) is assessed using the Beer Lambert Law on a ratio of the absorbance at 260 and 280 nm ($A_{260/280}$).

22. The optical measuring method of claim 17,
wherein positioning the liquid handling tip (4) with the liquid drop (2) attached according to step (iv) is improved in that the measurement signals (12) provided with the detector (10) and received by the processor (13) are maximized through moving the liquid handling tip (4) into at least one of an X-, Y-, and Z-direction of a Cartesian coordinate system of the liquid handling system (3).

23. The optical measuring method of claim 17,
wherein positioning the liquid handling tip (4) with the liquid drop (2) attached according to step (iv) is improved in that a quadrant-style photo detector (31) is utilized and the liquid handling tip (4) of the liquid handling system (3) is moved in an X-, Y-, and Z-direction of a Cartesian coordinate system until the measurement signal (12) of all four quadrants of the quadrant-style photo detector (31) are equalized.

24. The optical measuring method of claim 17,
wherein the optical measuring apparatus (1) comprises a shield (24) that encloses a detection space (25) and that comprises an opening (27), the liquid handling tip (4) being entered through the opening (26), and
wherein after positioning the liquid handling tip (4) with the liquid drop (2) attached according to step (iv), at least one of temperature and humidity of a gas atmosphere in the detection space (25) inside the shield (24) is controlled by at least one of a temperature regulation source (29) and a humidifying source (28).

25. The optical measuring method of claim 17,
wherein positioning the liquid handling tip (4) with the liquid drop (2) attached according to step (iv) is improved in that changing optics position is effected by moving the light source (8), its first optical elements (18) as well as the detector (10) with its second optical elements (19) with a dedicated X/Y/Z drive that is based on piezo elements.

* * * * *